April 8, 1958 H. C. SWIM Plant Pat. 1,694
ROSE PLANT
Filed May 8, 1957
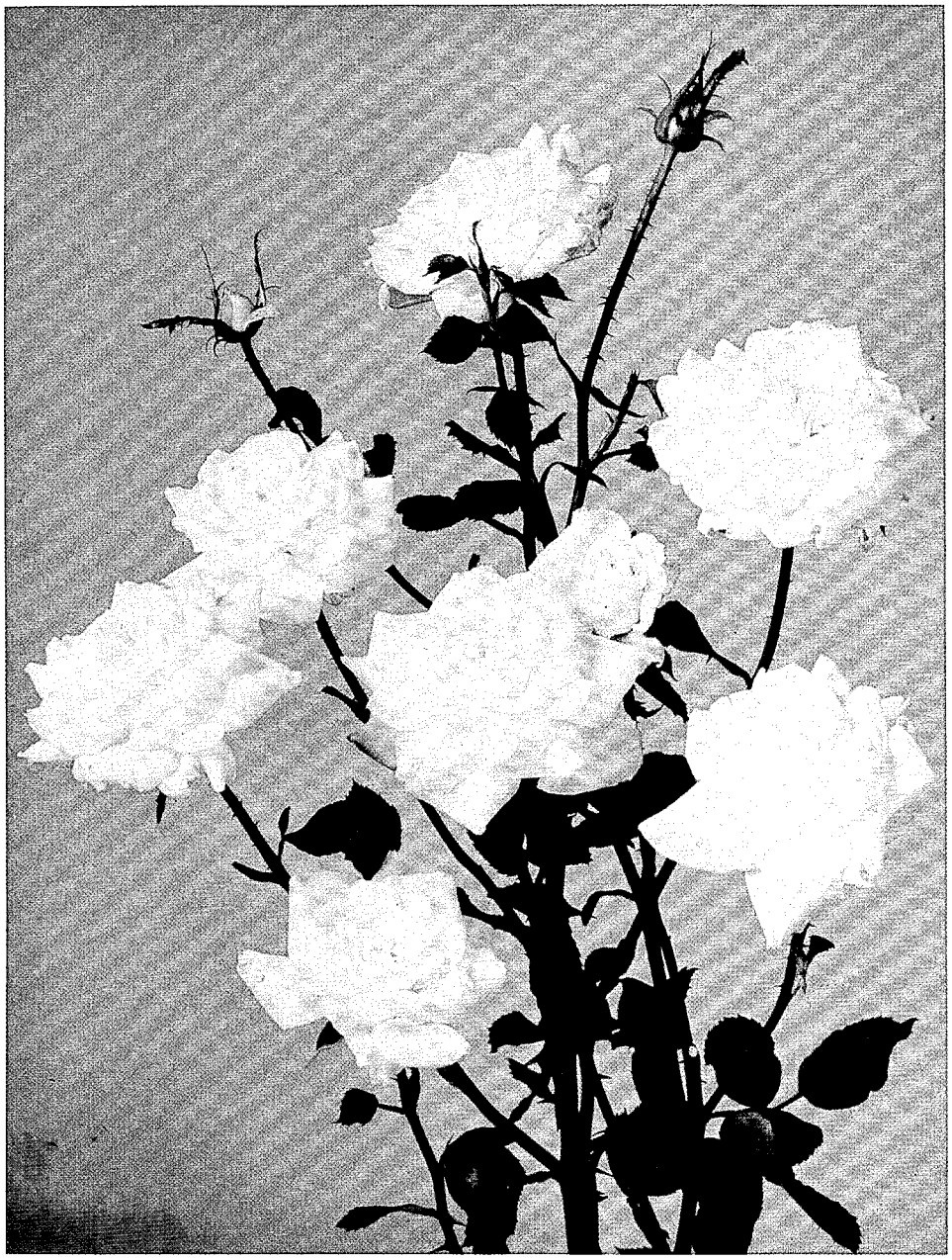
Inventor
H. C. Swim
By: Robb & Robb
Attorneys.

United States Patent Office

Plant Pat. 1,694

Patented Apr. 8, 1958

1,694

ROSE PLANT

Herbert C. Swim, Ontario, Calif., assignor to Armstrong Nurseries, Inc., Ontario, Calif., a corporation of California Application May 8, 1957, Serial No. 657,991

1 Claim. (Cl. 47—61)

The present invention relates to a new and distinct variety of rose plant of the hybrid polyantha class, which was originated by me by crossing an unnamed and unpatented variety with the variety "Goldilocks" (Plant Patent No. 672).

The unnamed variety referred to above was used as the pollen parent, and was characterized by being a rose of the floribunda type. Its plant was upright and moderately vigorous in habit, and its flowers were double and of a light yellow color, being borne in medium sized clusters, with each flower measuring from 3 to 4 inches in diameter.

The primary objective of the new variety was to combine the most desirable characteristics of the two parent varieties. This objective was fully achieved, along with other improvements, as evidenced by the following unique combination of characteristics which are predominant in the new variety:

(1) Moderately vigorous, compact and upright plant habit;

(2) Medium sized, dark green, glossy foliage;

(3) Medium sized, very double flowers, somewhat similar to those of the seed parent "Goldilocks";

(4) Better bud form than the buds of "Goldilocks";

(5) Bright yellow general color tonality of the flowers, similar to that of the flowers of the seed parent "Goldilocks"; and (6) Better color retention and less fading as the flower ages than in the flowers of "Goldilocks."

In comparison with its seed parent, "Goldilocks," the growth habit of the new variety is upright and more compact, as distinguished from the more spreading and open habit of this parent, and the foliage of the new variety is a somewhat darker green than that of this parent.

As compared with its unnamed pollen parent, the foliage of the new variety is smaller but more glossy; the flowers are slightly smaller; the flowers have considerably greater petalage; and the flower color is a darker yellow color.

The foregoing characteristics and distinctions definitely differentiate my new variety from its parents, as well as from all other varieties of its class of which I am aware, and a sexual reproduction of the new variety by budding, as performed at Ontario, California, shows that said characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgeway's Color Standards and Nomenclature (hereinafter abbreviated at "Ridgway"), as indicated:

Type: Bush; outdoor; seeding; for cut flowers and for garden decoration.

Class: Hybrid polyantha.

Breeding: Seedling.

*Seed parent.*—"Goldilocks."

*Pollen parent.*—An unnamed seedling.

Propagation: Holds its distinguishing characteristics through succeeding propagations by budding.

*Flower*

Locality where grown and observed: Ontario, California.

Flowers borne: Usually from 3 to 5 or more to stem; in regular, rounded clusters; on stems of from short to medium length and normal strength.

Quantity of bloom: Abundant, outdoors.

Continuity: Continuous during growing season.

Fragrance: From slight to moderate.

Bud:

*Peduncle.*—From short to average length; average caliper; erect; moderately smooth; some gland-tipped cilia; few prickles. Color—near Snuff Brown, Plate XXIX (Ridgway) on side exposed to sun.

*Before calyx breaks.*—Size—small. Form—short; globular; with foliaceous appendages and few gland-tipped cilia on the surface of the bud; usually with slender, bristle-like, foliaceous parts extending beyond the tip of the bud equal to ¼ or more of its length.

*As calyx breaks.*—Color—near Primrose Yellow, Plate 601/1, page 65 (Wilson).

*Sepals.*—Inner surface with fine, woolly tomentum; margins of alternate sepals lined with fine woolly tomentum; others lined with gland-tipped cilia.

*As first petal opens.*—Size—small. Form—globular. Color: outside—between Dresden Yellow, Plate 64/2, page 64 (Wilson) and Primrose Yellow, Plate 601/1, page 65 (Wilson); inside—near Primrose Yellow, Plate 601/1, page 65 (Wilson).

*Opening.*—Opens up well; is not retarded from opening by cold, hot, wet or dry weather.

Bloom:

*Size (when fully open).*—From small to average; from 2½ to 3¼ inches.

*Petalage.*—Double; from 60 to 66 petals, plus 10 to 12 petaloids; arranged regularly.

*Form.*—High-centered at first, but becoming high-centered-globular; petals being at first somewhat loosely cupped, with lateral margins reflexed slightly approximately ⅓ of upper portion of petal, and with lateral margins of outer petals usually rolled outward from ⅓ to ½ of length of petal, but becoming later at maturity more loosely cupped, with lateral margins of petals rolled strongly outward from ½ to ¾ of its length, and with lateral margins of outer petals sometimes rolled outward the entire length of the petal.

Petals:

*Texture.*—Medium thickness; moderately leathery.

*Appearance.*—Inside—satiny. Outside—satiny.

*Shape.*—Outside—broadly obovate, with apex flat, and usually with one or two notches. Intermediate—obovate, with apex rounded, and sometimes with one or two notches. Inside—narrowly obovate, with apex rounded, and sometimes with one or two notches.

This description of a newly opened flower was made from a rose grown outdoors in the month of October, at Ontario, California:

*Color.*—Outer petal: outside surface—near Primrose Yellow, Plate 601/2, page 65 (Wilson), with small area at base near attachment near Primrose Yellow, Plate 601, page 65 (Wilson); inside surface—near Primrose Yellow, Plate 601/1, page 65 (Wilson), with small area at base near attachment near Dresden Yellow, Plate 64/2, page 64 (Wilson). Intermediate petal: outside surface—between Empire Yellow, Plate 603, page 66 (Wilson) and Empire Yellow, Plate 603/1, page 66 (Wilson), with small area at base near attachment near Empire Yellow, Plate 603, page 66 (Wilson); inside surface—near Empire Yellow, Plate 603, page 66 (Wilson), with small area at base near attachment near Straw Yellow, Plate 604, page 67 (Wilson). Inner petal: outside surface—between Empire Yellow, Plate 603, page 66 (Wilson) and Straw Yellow, Plate 604, page 67 (Wilson); inside surface—between Empire Yellow, Plate 603, page 66 (Wilson) and Straw Yellow, Plate 604, page 67 (Wilson).

This description was made from a rose that was open for three days outdoors in the month of October, at Ontario, California:

*Color.*—Outer petal: outside surface—near Primrose Yellow, Plate 601/3, page 65 (Wilson), with small area at base near attachment near Empire Yellow, Plate 603/2, page 66 (Wilson); inside surface—near Primrose Yellow, Plate 601/2, page 65 (Wilson), with small area at base near Empire Yellow, Plate 603/1, page 66 (Wilson). Inner petal: outside surface—near Empire Yellow, Plate 603/1, page 66 (Wilson), with small area at base near attachment near Empire Yellow, Plate 603, page 66 (Wilson); inside surface—near Empire Yellow, Plate 603, page 66 (Wilson), with small area at base near attachment near Straw Yellow, Plate 604, page 67 (Wilson).

General color effect:

*Newly opened flower.*—Between Empire Yellow, Plate 603, page 66 (Wilson) and Straw Yellow, Plate 604, page 67 (Wilson).

*Three days open.*—Between Empire Yellow, Plate 603/1, page 66 (Wilson) and Straw Yellow, Plate 604/1, page 67 (Wilson).

Behaviour: Drop off cleanly; not particularly affected by cold, hot, wet or dry weather.

Flower longevity:

*On bush in garden.*—4 or 5 days in October.

*Cut roses grown outdoors and kept at livingroom temperatures.*—From 4 to 6 days in October.

*Reproductive organs*

Stamens: Very few; arranged irregularly about pistils; a few mixed with petaloids.

Filaments: From short to medium length; from 4 to 5 mm. in length; most with anthers. Color: near Lemon Yellow, Plate 4/2, page 4 (Wilson).

Anthers: Medium size; all open approximately at once. Color: upper side—margins near Indian Yellow, Plate 6/1, page 6 (Wilson), with remainder near Empire Yellow, Plate 603, page 66 (Wilson); under side—margins near Indian Yellow, Plate 6/1, page 6 (Wilson), with remainder near Empire Yellow, Plate 603, page 66 (Wilson).

Pollen: Very sparse. Color—near Indian Yellow, Plate 6/1, page 6 (Wilson).

Pistils: Few; approximately 30 in number.

Styles: Uneven; average length; from 5 to 8 mm. in length; thin caliper; somewhat loosely bunched. Color—near Uranium Green, Plate 63/2, page 63 (Wilson).

Stigma: Color—near Aureolin, Plate 3/1, page 3 (Wilson).

Ovaries: Usually most enclosed in calyx.

Hips: None.

Sepals: Permanent; medium length; recurved. Color: inside—near Light Grape Green, Plate XLI (Ridgway), masked by white woolly tomentum; outside—near Courge Green, Plate XVII (Ridgway).

Seeds: None.

*Plant*

Foliage:

*Leaves.*—Compound of usually 3 to 5 leaflets; from normal quantity to abundant; medium size; somewhat leathery; semi-glossy.

*Leaflets.*—Shape—ovoid, with apex acute. Base—round. Margin.—simply serrate.

*Color.*—Mature: upper surface—between Hellebore Green, Plate XVII (Ridgway) and Dark Dull Yellow-Green, Plate XXXII (Ridgway); under surface—near Asphodel Green, Plate XLI (Ridgway). Young: upper surface—near Cerro Green, Plate V (Ridgway); undersurface—between Grape Green, Plate XLI (Ridgway) and Asphodel Green, Plate XLI (Ridgway).

*Rachis (the supporting stem of the compound leaf).*—Average size. Upper side—grooved; with few stipitate glands on edges. Under side—with stipitate glands; with 2 or 3 prickles.

*Stipules.*—From short to medium length; from narrow to medium width; with medium length points turning out at an angle of more than 45°.

*Disease resistance.*—Better than average resistance to mildew, as compared with other varieties grown under comparable cultural conditions in Ontario, California.

Growth:

*Habit.*—Upright.

*Growth.*—Free.

*Canes.*—Medium caliper.

*Main stems.*—Color—between Courge Green, Plate XVII (Ridgway) and Biscay Green, Plate XVII (Ridgway). Large prickles—from few to several; from medium length to long; straight; with medium length, narrow base; color—near Verona Brown, Plate XXIX (Ridgway). Small prickles—none. Hairs—none.

*Branches.*—Color—near Parrot Green, Plate VI (Ridgway). Large prickles—from few to several; medium length; almost straight; with medium length, narrow base; color—near Lime Green, Plate XXXI (Ridgway). Small prickles—none. Hairs—none.

*New shoots.*—Color—between Kildare Green, Plate XXXI (Ridgway) and Absinthe Green, Plate XXXI (Ridgway), overlaid with Walnut Brown, Plate XXVIII (Ridgway). Large prickles—from few to several; from moderate length to long; almost straight; hooked very slightly downward; with medium length, narrow base; color—near Light Yellowish Olive, Plate XXX (Ridgway). Small prickles—none. Hairs—none.

I claim:

A new and distinct variety of rose plant of the hybrid polyantha class, substantially as herein shown and described, characterized particularly as to novelty by its moderately vigorous, compact and upright habit of growth, its dark green glossy foliage of medium size, its very double flowers of medium size, good bud form, the bright yellow general color tonality of its flowers, and its long color retention without fading as the flowers age.

No references cited.